US012090256B2

(12) United States Patent
Radwanski et al.

(10) Patent No.: US 12,090,256 B2
(45) Date of Patent: Sep. 17, 2024

(54) SYSTEMS AND METHODS FOR PLATELET FILTRATION USING AN ADDITIVE

(71) Applicant: Fenwal, Inc., Lake Zurich, IL (US)

(72) Inventors: Katherine N. Radwanski, Highland Park, IL (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 957 days.

(21) Appl. No.: 16/488,724

(22) PCT Filed: Apr. 20, 2017

(86) PCT No.: PCT/US2017/028483
§ 371 (c)(1),
(2) Date: Aug. 26, 2019

(87) PCT Pub. No.: WO2018/194602
PCT Pub. Date: Oct. 25, 2018

(65) Prior Publication Data
US 2020/0030503 A1 Jan. 30, 2020

(51) Int. Cl.
*A61M 1/02* (2006.01)
*A61J 1/10* (2006.01)
*A61M 1/36* (2006.01)

(52) U.S. Cl.
CPC ........ *A61M 1/0218* (2014.02); *A61M 1/3622* (2022.05); *A61M 1/36225* (2022.05);
(Continued)

(58) Field of Classification Search
None
See application file for complete search history.

(56) References Cited

U.S. PATENT DOCUMENTS 5,427,509 A * 6/1995 Chapman ........ A61M 1/362261
604/153
6,312,607 B1 11/2001 Brown et al.
(Continued)

FOREIGN PATENT DOCUMENTS

WO WO-2016172645 A1 * 10/2016 ........... A01N 1/0263

OTHER PUBLICATIONS

International Search Report and Written Opinion from the International Searching Authority for International Application No. PCT/US2017/028483, dated Jan. 11, 2018 (12 pages).

*Primary Examiner* — Jonathan M Peo
(74) *Attorney, Agent, or Firm* — Cook Alex Ltd.

(57) ABSTRACT

Systems and methods are provided for collecting a platelet product from a fluid including platelets and plasma. Platelet-rich plasma is separated from at least a portion of another constituent of the fluid and then may be further separated into concentrated platelets and platelet-poor plasma, with the concentrated platelets being resuspended. Separated platelets are conveyed through a size exclusion filter and into a platelet storage container. The size exclusion filter is configured to remove platelet clumps and/or particles larger than a platelet from the separated platelets. Subsequently, an additive is conveyed through the size exclusion filter and into the platelet storage container. Conveying additive through the size exclusion filter improves platelet recovery in the platelet product by displacement of separated platelets with the additive and may also break up any platelet clumps that are present in the size exclusion filter.

20 Claims, 7 Drawing Sheets

(52) U.S. Cl.
CPC .... *A61M 1/362265* (2022.05); *A61M 1/3693* (2013.01); *A61J 1/10* (2013.01); *A61M 2202/0427* (2013.01); *A61M 2205/123* (2013.01); *A61M 2205/125* (2013.01); *A61M 2205/7545* (2013.01)

(56) References Cited

U.S. PATENT DOCUMENTS

| | | |
|---|---|---|
| 6,582,349 B1 | 6/2003 | Cantu et al. |
| 8,192,386 B2 | 6/2012 | Min |
| 8,808,217 B2 | 8/2014 | Ohashi et al. |
| 8,852,140 B2 | 10/2014 | Barry, Jr. et al. |
| 8,920,659 B2 | 12/2014 | Hillyer et al. |
| 9,402,866 B2 | 8/2016 | Radwanski et al. |
| 2006/0086666 A1 | 4/2006 | Mari et al. |
| 2012/0111807 A1* | 5/2012 | Hillyer ................ A61M 1/0281 210/806 |
| 2012/0175313 A1* | 7/2012 | Barry, Jr. ............ A61M 1/3672 210/96.1 |
| 2014/0037750 A1* | 2/2014 | Radwanski ......... A61M 1/3692 424/601 |
| 2015/0056602 A1 | 2/2015 | Radwanski et al. |

* cited by examiner

SYSTEMS AND METHODS FOR PLATELET FILTRATION USING AN ADDITIVE

This application is a U.S. national stage application of PCT Patent Application Serial No. PCT/US2017/028483, filed Apr. 20, 2017, which was published on Oct. 25, 2018 as PCT Patent Application Publication No. WO 2018/194602 A1 and which is hereby incorporated herein by reference.

TECHNICAL FIELD

The present disclosure is directed to systems and methods for collecting blood platelets. More particularly, the present disclosure is directed to systems and methods for improving the yield and quality of collected platelets using a filter and an additive.

BACKGROUND

Whole blood is made up of various cellular components such as red cells, white cells, and platelets suspended in its liquid component, plasma. Whole blood can be separated into its constituent components (cellular or liquid), and the desired separated component can be administered to a patient in need of that particular component. For example, platelets can be removed from the whole blood of a blood source, collected, and later administered to a cancer patient whose ability to "make" platelets has been compromised by chemotherapy or radiation treatment.

Automated blood separation systems are used to collect large numbers of platelets. Automated systems perform the separation steps necessary to separate platelets from whole blood in a sequential process. Automated systems draw whole blood from the source, separate out the desired platelets from the drawn blood, and optionally return the remaining red blood cells and plasma to the blood source, all in a sequential flow loop. Large volumes of whole blood can be processed using an automated "on-line" system. Due to the large processing volumes, large yields of concentrated platelets can be collected.

Commonly, platelets are collected by introducing whole blood into a centrifuge chamber in which the whole blood is separated into its constituent components, including platelets, based on the size and densities of the different components. This requires that the whole blood be passed through a centrifuge after it is withdrawn from (and, optionally, before one or more separated blood components is returned to) the blood source. Typical blood processing systems thus include a permanent, reusable centrifuge assembly containing the hardware (drive system, pumps, valve actuators, programmable controller, and the like) that pumps and separates the blood, and a disposable, sealed, and sterile fluid processing assembly that is mounted cooperatively on the hardware. The centrifuge assembly spins a disposable centrifuge chamber of the fluid processing assembly during a collection procedure, thereby separating the blood into its constituent components. The separated platelets are typically reconstituted in a liquid storage medium or additive, such as plasma and/or a synthetic storage solution, for storage until needed for transfusion to a patient.

For the stored platelets to be suitable for later administration, they must substantially retain their viability and platelet function. A number of interrelated factors may affect platelet viability and function during storage. Some of these factors include the anticoagulant used for blood collection, the method used to prepare the platelets, the type of storage container used, and the medium in which the platelets are stored.

Currently, platelets may be stored for five or even seven days at 22° C. After seven days, however, platelet function may become impaired. In addition to storage time, other storage conditions have been shown to affect platelet metabolism and function, including: pH, storage temperature, total platelet count, plasma volume, agitation during storage, platelet concentration, and the presence of platelet clumps in the final platelet product.

SUMMARY

There are several aspects of the present subject matter which may be embodied separately or together in the devices, systems, and methods described and/or claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto or later amended.

In one aspect, a disposable processing circuit includes a processing chamber configured to receive a fluid including plasma and platelets and associable with a separation device of a reusable hardware apparatus for separation of platelets from at least a portion of another constituent of a fluid including plasma and platelets. The disposable processing circuit also includes a size exclusion filter in downstream fluid communication with the processing chamber and configured to remove platelet clumps from separated platelets conveyed therethrough from the processing chamber. A platelet storage container is provided in downstream fluid communication with the size exclusion filter and configured to receive filtered platelets from the size exclusion filter, while an additive container is provided in upstream fluid communication with the size exclusion filter.

In another aspect, a method is provided for collecting platelets. The method includes providing a fluid from a fluid source including plasma and platelets, and separating platelets from at least a portion of another constituent of the fluid. The separated platelets are conveyed through a size exclusion filter to remove platelet clumps from the separated platelets, with the filtered platelets being collected in a platelet storage container. An additive is then conveyed through the size exclusion filter and into the platelet storage container.

DETAILED DESCRIPTION OF THE ILLUSTRATED EMBODIMENTS

The embodiments disclosed herein are for the purpose of providing an exemplary description of the present subject matter. They are, however, only exemplary and not exclusive, and the present subject matter may be embodied in various forms. Therefore, specific details disclosed herein are not to be interpreted as limiting the subject matter as defined in the accompanying claims.

The present disclosure is directed to methods and systems for collecting blood platelets in a platelet storage media or additive. The platelet storage media or additive may be variously configured without departing from the scope of the present disclosure and may include plasma and/or a synthetic storage fluid, which is commonly referred to as a platelet additive solution or "PAS." Platelet products described herein include the platelet storage media (typically PAS and plasma) and the platelets stored therein. If PAS is used, it typically replaces 60-70% or more of the plasma in the platelet constituent, thereby decreasing the amount of plasma required to suspend and store the platelets. The use of PAS in addition to plasma as a platelet storage media may be advantageous for a number of reasons (e.g., the reduced incidence of allergic transfusion reactions resulting from platelets stored in PAS), but it should be understood that the term "additive" as used herein encompasses both plasma and non-plasma fluids and combinations thereof unless stated to the contrary.

Exemplary Separation System

Figure 1:
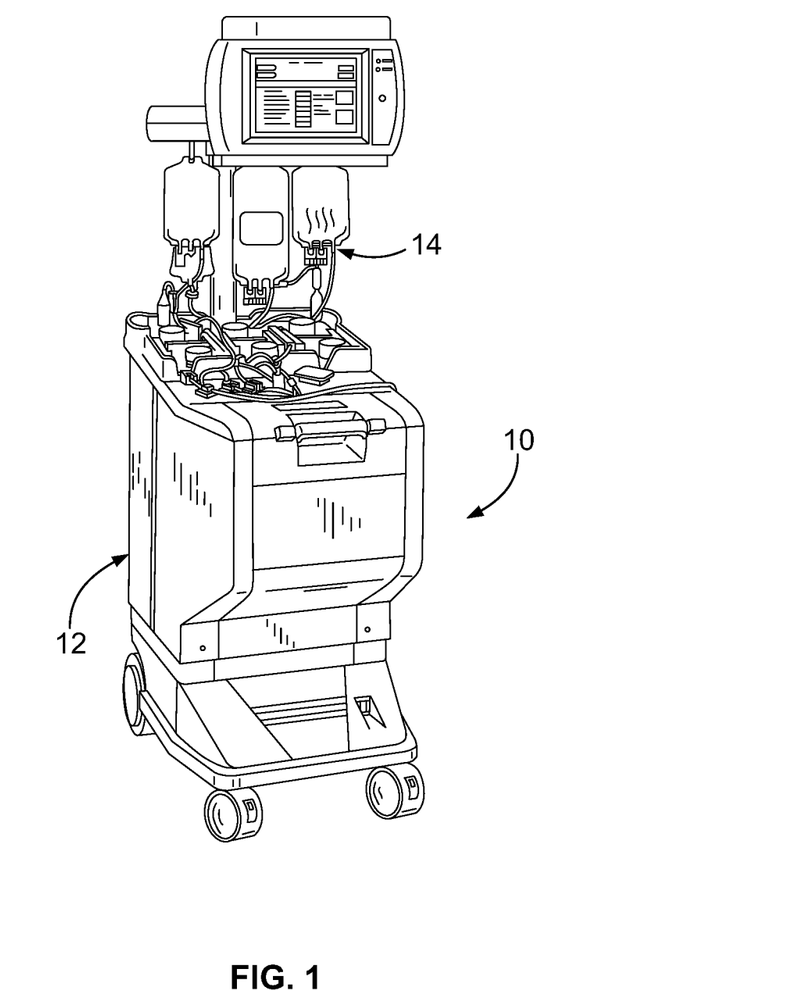
FIG. 1 is a perspective view of an exemplary automated separation system that may be used in the collection and other processing steps of platelets in accordance with an aspect of the present disclosure.
Figure 2:
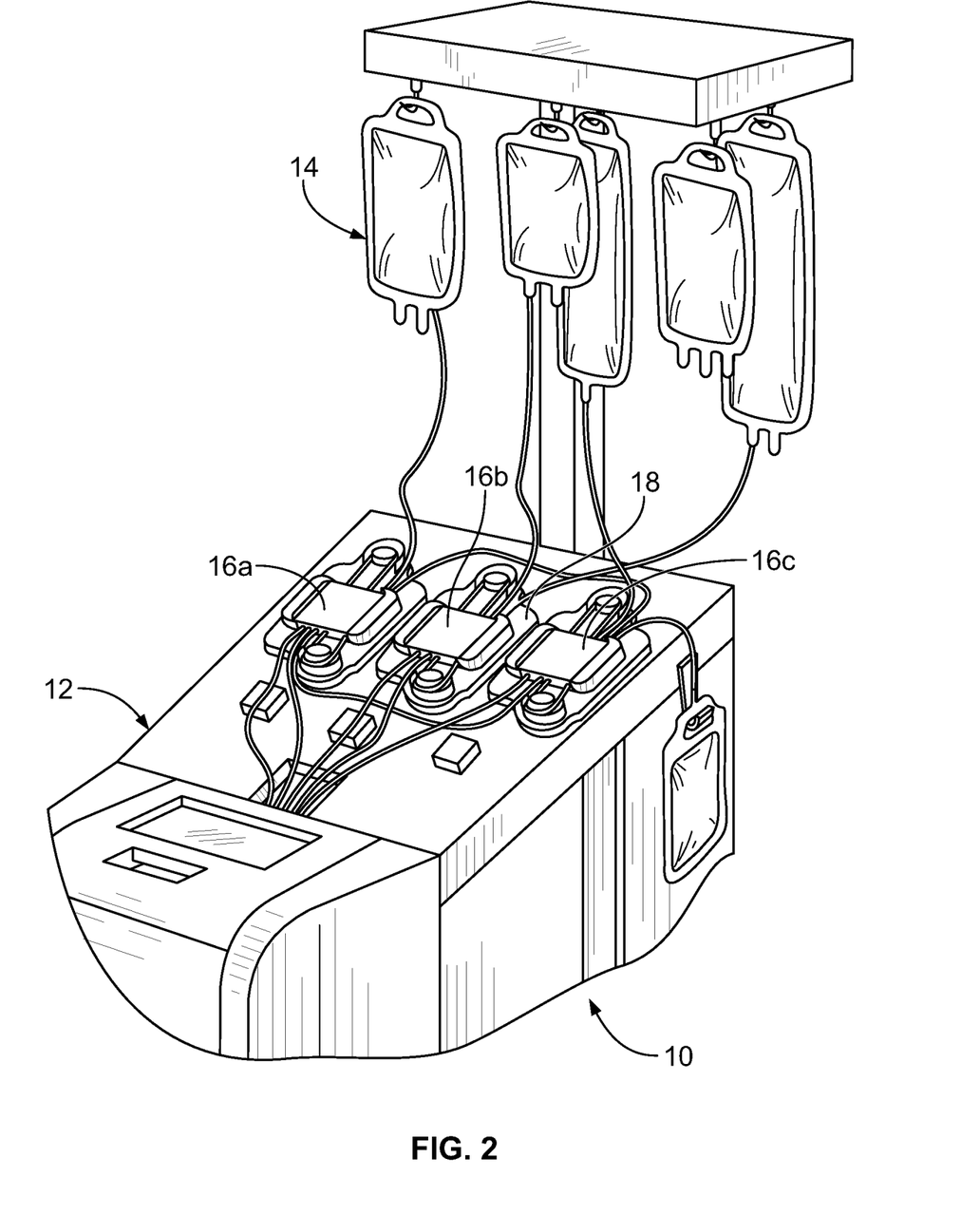
FIG. 2 is a detail view of a portion of the separation system of FIG. 1.

Platelets for storage may be obtained by separating platelet-rich plasma from a biological fluid including plasma and platelets (including, but not limited to, whole blood). FIGS. 1 and 2 show a representative separation system 10 useful in the separation and collection of platelets and the delivery of the additive, as described herein. The illustrated separation system 10 is similar to the AMICUS® separation system, available from Fenwal, Inc. of Lake Zurich, Illinois, which is an affiliate of Fresenius Kabi AG of Bad Homburg, Germany, and which is described in greater detail in U.S. Pat. Nos. 5,427,509; 6,312,607; 6,582,349; and 8,192,386, the entire contents of all of which are incorporated herein by reference. However, it should be understood that the illustrated separation system 10 is merely exemplary and that the configuration of the separation system may vary without departing from the scope of the present disclosure.

Figure 3:
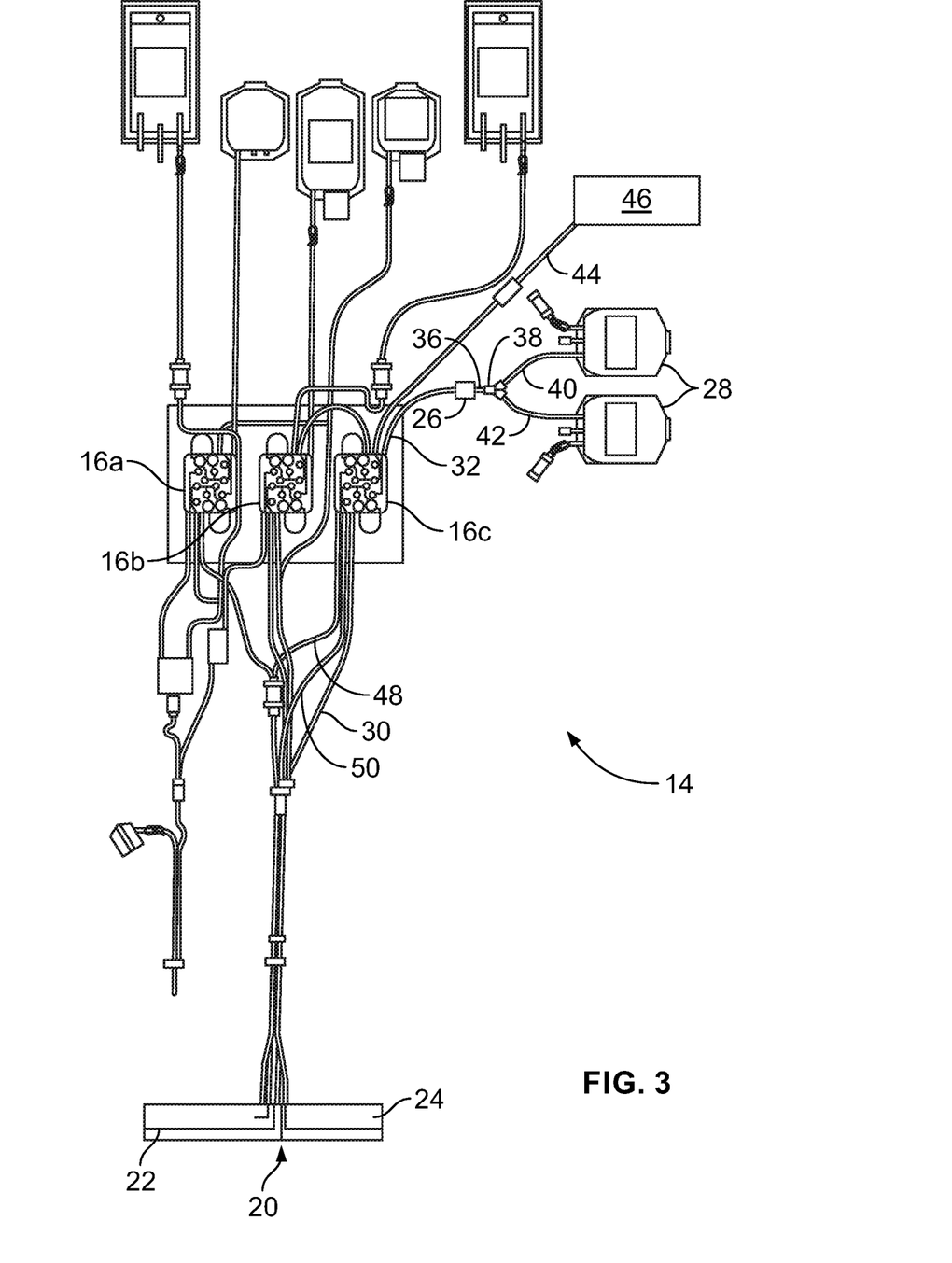
FIG. 3 is a top plan view of a disposable processing circuit of the separation system of FIGS. 1 and 2.

The separation system 10 of FIGS. 1 and 2 includes a hardware component or apparatus 12 and a disposable processing kit or circuit 14 mounted thereon. The disposable circuit 14 includes an access device (e.g., a needle) for accessing the blood or other biological fluid of a fluid source. The disposable circuit 14 also includes a plurality of containers for holding fluid (e.g., anticoagulant and saline) and tubing segments defining flow paths for movement of the fluid, its separated constituents, and other fluids through the fluid circuit 14. The illustrated disposable processing circuit 14 includes one or more cassettes (shown in FIG. 2 as three cassettes 16a, 16b and 16c), which interface with a front panel 18 of the hardware apparatus 12. Each cassette 16a, 16b, and 16c includes flow paths and valve stations. The front panel 18 of the hardware apparatus 12 includes a series of valves under the control of a pre-programmed controller of the hardware apparatus 12, which selectively allow and restrict flow through the flow paths of the cassettes 16a, 16b, 16c and ultimately through the tubing segments of the disposable circuit 14.

In the illustrated embodiment, a rotating centrifuge is housed within the hardware apparatus 12 to receive a processing chamber 20 (FIG. 3) of the disposable circuit 14. The illustrated processing chamber 20 has first and second stages 22 and 24 wherein fluid or fluid components are separated under the influence of centrifugal force. While a centrifuge is employed by the illustrated system 10, it is within the scope of the present disclosure for a separator based on a different separation principle to also be used.

The disposable circuit 14 further includes a size exclusion filter 26 in upstream fluid communication with one or more platelet storage containers 28, such that any fluid flowing into the platelet storage container(s) 28 must first flow through the size exclusion filter 26. In the illustrated embodiment, the size exclusion filter 26 is in downstream fluid communication with one of the cassettes 16c, thus being interposed between that cassette 16c and the one or more platelet storage containers 28. The size exclusion filter 26 is configured to remove platelet clumps from fluid flowing through the size exclusion filter 26. In an alternative embodiment, the size exclusion filter 26 may be configured to remove particles greater than the size of a platelet (e.g., red blood cells and white blood cells, along with platelet clumps) from fluid flowing through the size exclusion filter 26. By flowing a platelet-containing substance through the size exclusion filter 26, platelet clumps are prevented from flowing into the platelet storage container(s) 28. This is advantageous for several reasons, as platelet clumps are known to decrease the quality of the stored platelet product (as aggregated products consume more glucose and produce more lactate) and interfere with post-processing steps, such as pathogen inactivation. Additionally, when performing flow cytometry-based enumeration of leukocytes, platelet aggregates (which are naturally autofluorescent) may appear in the leukocyte gate and be incorrectly counted as leukocytes, thereby artificially increasing the reported leukocyte content in the platelet product.

The hardware apparatus 12 may include a programmable controller that is pre-programmed with one or more selectable protocols. A user/operator may select a particular processing protocol to achieve a desired outcome or objective, including, for example, to obtain a platelet product having a pre-determined volume. The pre-programmed selectable protocol(s) may be based on one or more fixed and/or adjustable parameters, including, but not limited to, the volume of fluid being processed, the volume of additive used or added to the platelets during processing, the desired platelet concentration and/or the desired platelet yield, the processing time/duration of a given procedure, and/or the desired volume of final platelet product.

During a particular processing procedure, the pre-programmed controller may operate the centrifuge and processing chamber 20 associated therewith to separate fluid (such as anticoagulated whole blood) into its various components, as well as operate one or more pumps of the hardware apparatus 12 to move biological fluid, components of the biological fluid, and non-biological fluids through the disposable circuit 14. This may include, for example, initiating and causing the centrifugal separation of platelet-rich plasma from whole blood (or another biological fluid including plasma and platelets) in the first stage 22 of the processing chamber 20 and pumping at least a portion of the platelet-rich plasma out of the processing chamber 20 via a tubing segment 30. The platelet-rich plasma flows from the tubing segment 30 into and through one of the cassettes 16c, with the valves of the hardware apparatus 12 being actuated by the controller to direct the flow of platelet-rich plasma through the cassette 16c. The platelet-rich plasma exits the cassette 16c via another tubing segment 32 connected to the size exclusion filter 26 of the disposable circuit 14, flows through the size exclusion filter 26, and into a platelet storage container 28. The controller may subsequently control one or more pumps of the hardware apparatus 12 to pump additive through the size exclusion filter 26 (in the same direction of flow experienced by the platelet-rich plasma) to combine with the filtered platelet-rich plasma in the platelet storage container 28 as a platelet product. The various processing steps performed by the devices of the hardware apparatus 12 under command of the controller may occur separately, in series, simultaneously, or any combination of these.

Exemplary Single Stage Separation and Collection Procedure

Once an operator has selected the desired protocol, entered the necessary parameters, and mounted the processing circuit 14 to the hardware apparatus 12, collection of platelets may commence with biological fluid being conveyed into and through the processing circuit 14. This may be achieved in any of a number of ways, which may include the controller of the hardware apparatus 12 controlling one or more pumps of the hardware apparatus 12 to draw fluid into the processing circuit 14 from a fluid source, such as a blood bag.

The biological fluid is conveyed through the processing circuit 14 and directed through at least one of the cassettes 16a, 16b, 16c (with the controller controlling valves of the hardware apparatus 12 to direct flow through the cassette or cassettes) and into the first stage 22 of the processing chamber 20. The controller controls the centrifuge of the hardware apparatus 12 to rotate about a rotational axis at a rate that is sufficient to cause the platelets of the fluid to separate from another constituent of the fluid. In the illustrated example, platelet-rich plasma is separated from the other constituents of the biological fluid (red blood cells, if the fluid is whole blood) in the first stage 22 of the processing chamber 20. The second stage 24 of the processing chamber 20 is not used in platelet separation and collection in such an embodiment, so it may be loaded with an amount of fluid (e.g., saline) to balance the processing chamber 20 and centrifuge during use. However, in other embodiments in which the second stage 24 is used (as will be described in greater detail), the second stage 24 may remain available for fluid flow and separation (e.g., for the inflow of platelet-rich plasma and the outflow of a separated component, such as platelet-poor plasma).

Figure 4:
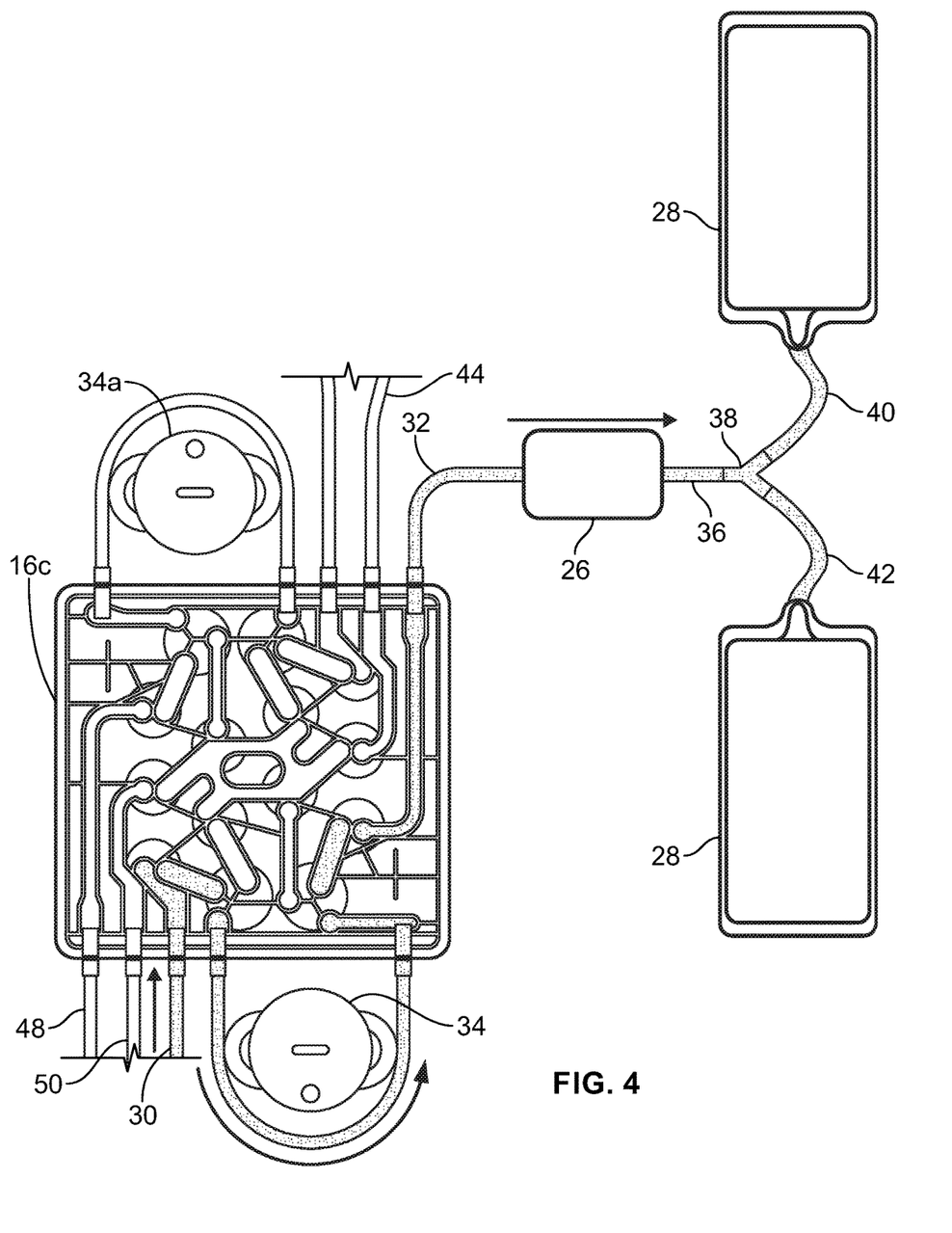
FIGS. 4 and 5 are detail views of a portion of the separation system of FIGS. 1 and 2 during different phases of an exemplary platelet separation and collection procedure according to an aspect of the present disclosure.

The platelet-rich plasma exits the first stage 22 of the processing chamber 20 and is conveyed through a tubing segment 30 to one of the cassettes 16c (FIG. 4). The other constituents of the fluid exit the first stage 22 through a different tubing segment and may be collected for further processing or as a waste product or may be returned to the fluid source. In one embodiment, at least a portion of one of the separated components may remain within the processing chamber 20 following separation.

The controller operates selected valves of the hardware apparatus 12 to direct flow of the platelet-rich plasma through the cassette 16c and out a second tubing segment 32, with the controller operating a pump 34 to convey the platelet-rich plasma into, through, and out the cassette 16c.

The second tubing segment 32 includes an inline size exclusion filter 26, which is configured to prevent the flow of platelet clumps and/or particles larger than a platelet, as described previously. Thus, by flowing the platelet-rich plasma through the size exclusion filter 26, platelet clumps and/or particles larger than a platelet (depending on the configuration of the size exclusion filter 26) are prevented from exiting the size exclusion filter 26, thereby improving the quality of the collected platelet product in various ways, which are described above. If platelet clumps are present in a platelet product, it is conventional to "rest" the product, which tends to lead to reduced oxygen levels, thereby promoting glycolysis and a resulting drop in pH.

The size exclusion filter 26 could be replaced with a leukoreduction filter, which would also function to remove platelet clumps from the separated platelet-rich plasma. However, it may be preferred to employ a size exclusion filter 26 for various reasons. For example, leukoreduction filters tend to be significantly more expensive than size exclusion filters. Additionally, a leukoreduction filter may not be as well-suited to releasing platelets upon the filter being flushed as a size exclusion filter (as will be described in greater detail).

A third tubing segment 36 is connected to the downstream end of the size exclusion filter 26 to direct the filtered platelet-rich plasma into a platelet storage container 28. In the illustrated embodiment, the third tubing segment 36 includes a joint 38, which splits the third tubing segment 36 into two branches 40 and 42, each having an associated platelet storage container 28. In other embodiments, there may be only one platelet storage container 28 or more than two platelet storage containers 28.

Figure 5:
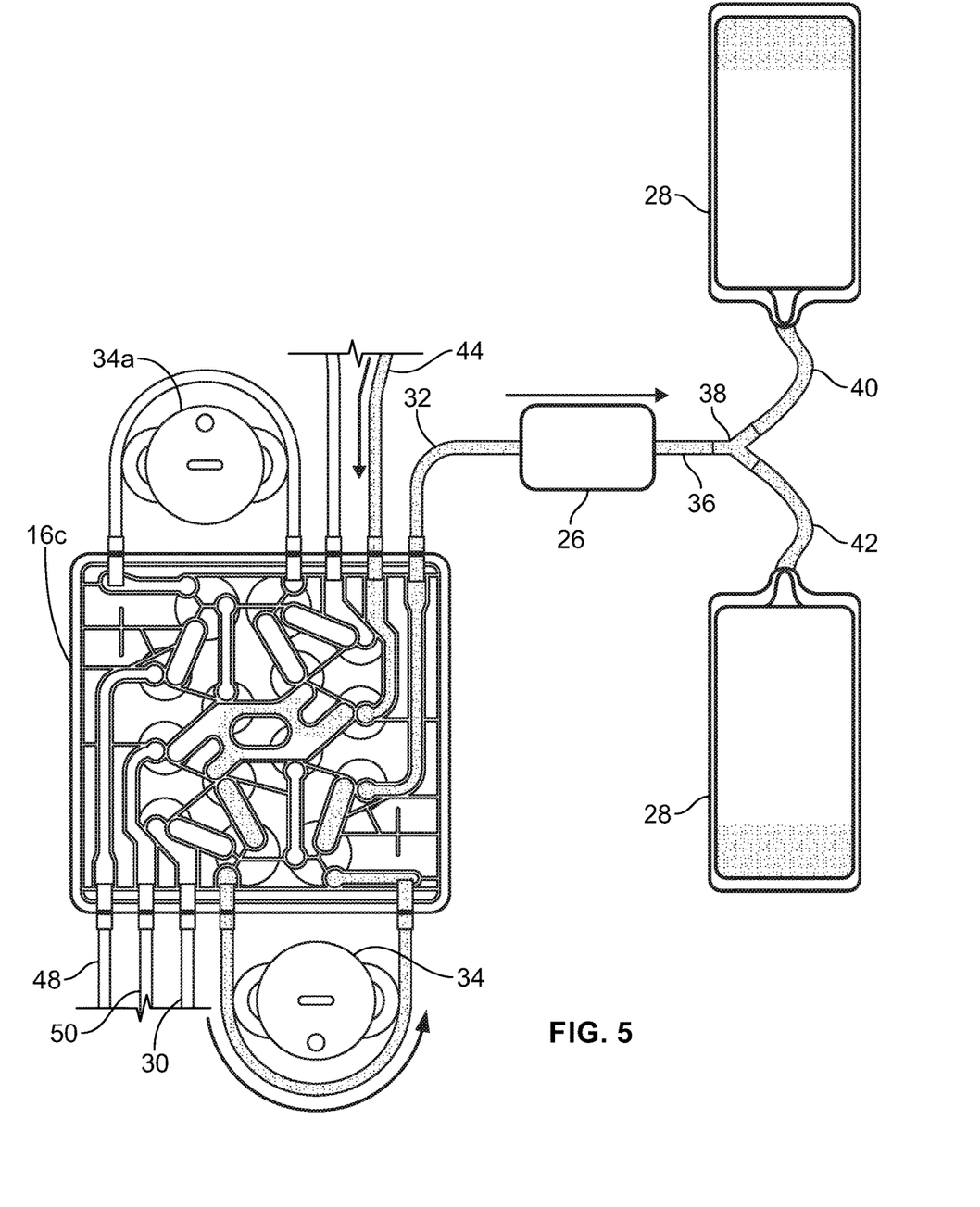

When all of the platelet-rich plasma to be filtered has passed through the size exclusion filter 26, the controller reconfigures the valves of the hardware apparatus 12 to define a different flow path through the cassette 16c (FIG. 5). The new valve configuration defines a flow path through the cassette 16c between a tubing segment 44 connected to an additive container 46 (FIG. 3) and the second tubing segment 32. The additive container 46 may be integrally formed with the remainder of the processing circuit 14 as part of a closed system or may be separately provided and connected to the circuit 14 (using a sterile docking port or spiked connector, for example) prior to use.

In one embodiment, the additive container 46 is provided with an amount of a synthetic PAS, but it is also within the scope of the present disclosure for the additive container 46 to be empty at the start of the procedure. In such an embodiment, plasma separated from the fluid in the processing chamber 20 (e.g., in the second stage 24) is directed into the additive container 46, with the plasma serving as an additive. According to yet another embodiment, a plurality of additive containers may be provided, with at least one including a synthetic PAS and at least another one being configured to receive separated plasma.

Regardless of the nature of the additive, the controller operates one or more of the pumps of the hardware apparatus (illustrated in FIG. 5 as a single pump 34) to convey additive through the tubing segment 44, into and through the cassette 16c, and out of the cassette 16c via the second tubing segment 32. The additive flows through the size exclusion filter 26 and into the platelet storage container(s) 28, where it mixes with the filtered platelet-rich plasma as a final platelet product. If a plurality of additive containers are provided, additive from the different containers may be sequentially or simultaneously conveyed through the size exclusion filter 26. Flushing the size exclusion filter 26 with the additive improves platelet recovery in the final platelet product by displacement of platelet-rich plasma with the additive and may also break up platelet clumps that may be present in the size exclusion filter 26, thereby increasing platelet yield.

With a suitable amount of additive in the platelet storage container(s) 28, the procedure may end or continue with additional processing (e.g., pathogen inactivation of the final platelet product).

Exemplary Double Stage Separation and Collection Procedure

It should be understood that the foregoing procedure is particular to the system 10 of FIGS. 1 and 2, but that the present disclosure is not limited to this particular method or a procedure employing such a system. In other embodiments, any of a number of phases of the preceding procedure may vary without departing from the scope of the present disclosure, provided that the separated platelets are conveyed through a size exclusion filter 26, followed by additive being conveyed through the size exclusion filter 26 to loosen clumped platelets and flush them into a location where the additive and flushed platelets are mixed with the filtered platelets.

For example, according to one variation of the preceding exemplary procedure, platelets may pass through both stages 22 and 24 of the processing chamber 20 before being conveyed through the size exclusion filter 26.

As described above with respect to the single stage procedure, once an operator has selected the desired (double stage) protocol, entered the necessary parameters, and mounted the processing circuit 14 to the hardware apparatus 12, collection of platelets may commence with biological fluid being conveyed into and through the processing circuit 14.

The biological fluid is conveyed through the processing circuit 14 and directed through at least one of the cassettes 16a, 16b, 16c (with the controller controlling valves of the hardware apparatus 12 to direct flow through the cassette or cassettes) and into the first stage 22 of the processing chamber 20. The controller controls the centrifuge of the hardware apparatus 12 to rotate about a rotational axis at a rate that is sufficient to cause the platelets of the fluid to separate from another constituent of the fluid (e.g., platelet-rich plasma being separated from red blood cells, if the fluid is whole blood) in the first stage 22 of the processing chamber 20.

Figure 6:
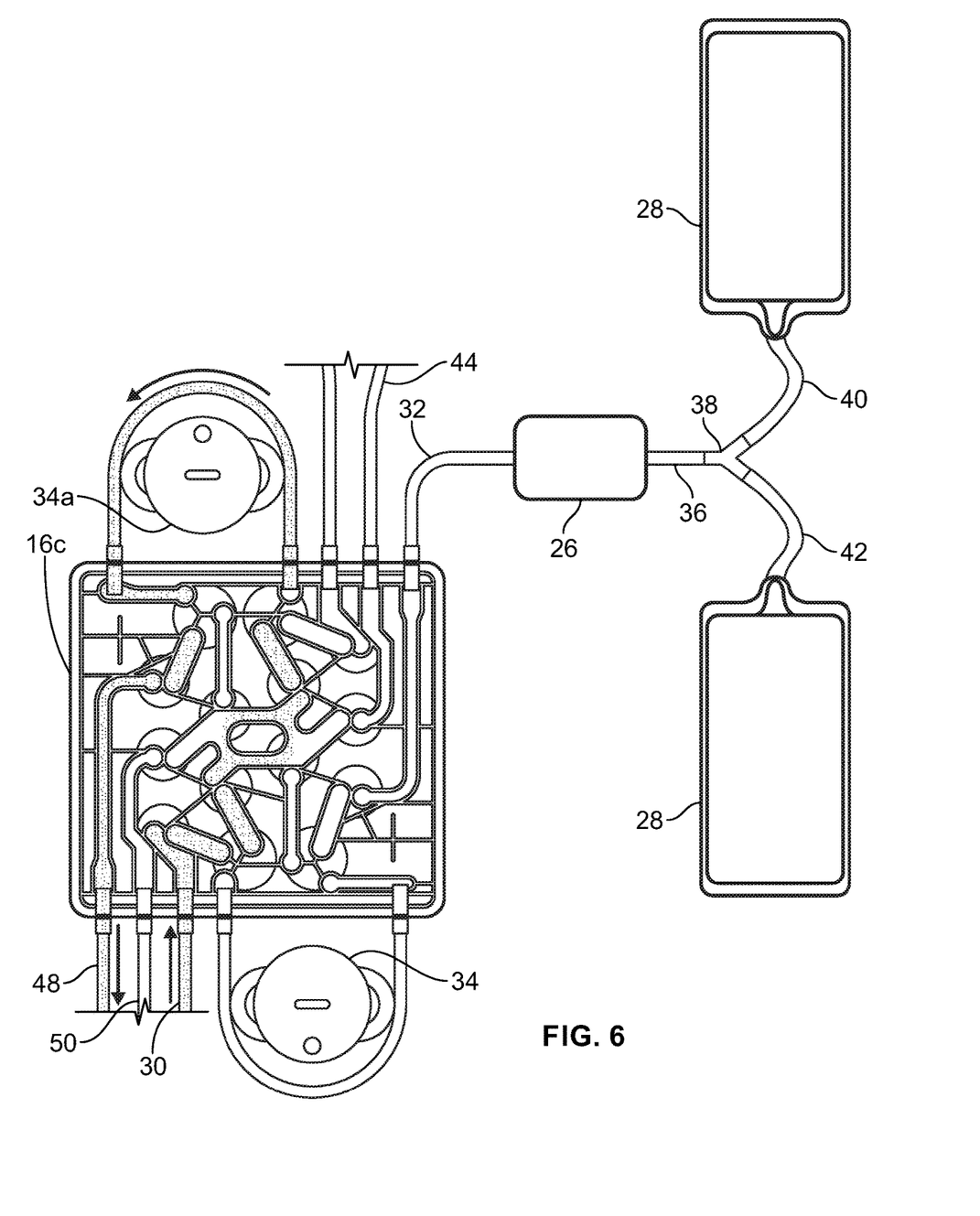
FIGS. 6 and 7 are detail views of a portion of the separation system of FIGS. 1 and 2 during different phases of another embodiment of an exemplary platelet separation and collection procedure according to an aspect of the present disclosure.

The separated platelets exit the first stage 22 via the tubing segment 30 and flow to one of the cassettes 16c, as in the single stage procedure. However, rather than being directed through the cassette 16c and then through the size exclusion filter 26 (as in FIG. 4), the controller instead operates a pump 34a and selected valves of the hardware apparatus 12 to direct flow of the platelets out of the cassette 16c via a tubing segment 48 leading into the second stage 24 of the processing chamber 20 (FIG. 6). As the platelets are being conveyed into the second stage 24, the other constituents of the fluid may exit the first stage 22 through a different tubing segment and may be collected for further processing or as a waste product or may be returned to the fluid source.

The rotation of the processing chamber 20 within the centrifuge causes the platelets entering the second stage 24 of the processing chamber 20 to be further concentrated by separating them from another fluid component. For example, if the fluid flowing into the second stage 24 is platelet-rich plasma, concentrated or pelleted platelets are separated from (platelet-poor) plasma. The fluid component separated from the platelets may flow out of the second stage 24 while platelets continue to accumulate in the second stage 24. In one embodiment, platelet-poor plasma (as the fluid component separated from the platelets in the second stage 24) is conveyed out of the second stage 24 and into a plasma or additive container, which may correspond to the additive container 46 or a different container.

Eventually (e.g., once the desired amount of platelets have been accumulated in the second stage 24 or once a predetermined amount of fluid has been processed), the controller may transition to a phase in which the platelets in the second stage 24 are resuspended. The platelets may be resuspended using platelet-poor plasma separated from the platelets during the preceding phase, a synthetic PAS, or a different fluid or combination of fluids.

Figure 7:
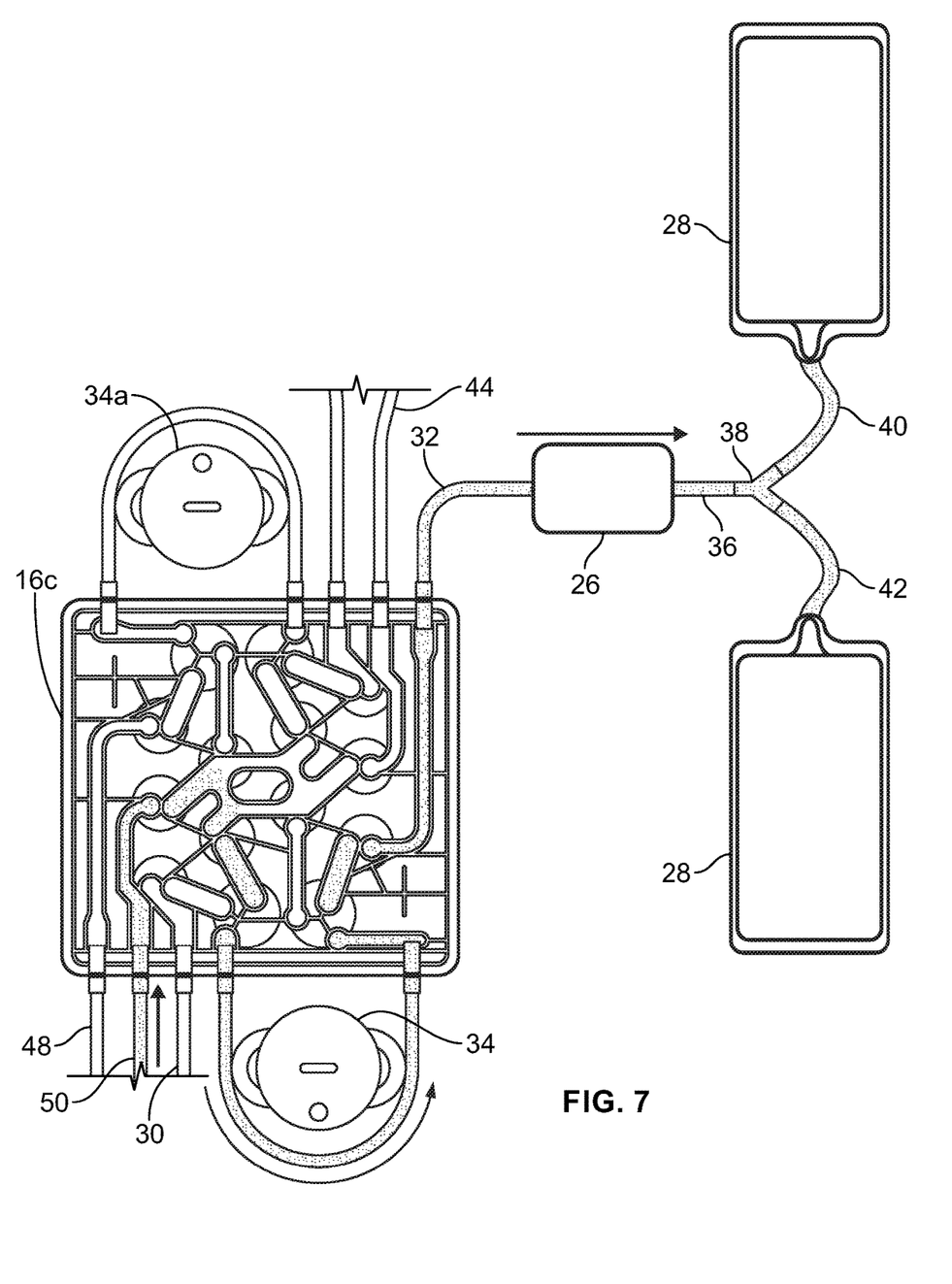

The resuspended platelets are then conveyed out of the second stage 24 of the processing chamber 20 and into the cassette 16c via a tubing segment 50 of the processing circuit 14. The controller operates selected valves of the hardware apparatus 12 to direct flow of the resuspended platelets through the cassette 16c and out the second tubing segment 32 (FIG. 7), with the controller operating a pump 34 to convey the resuspended platelets into, through, and out the cassette 16c.

The resuspended platelets pass through the size exclusion filter 26 of the second tubing segment 32, the third tubing segment 36, and the joint 38 and one of the branches 40 and 42 (if provided), to a platelet storage container 28, as described above with respect to the platelet-rich plasma in the single stage procedure. Passing separated platelets through a size exclusion filter 26 is particularly advantageous when the separated platelets comprise resuspended platelets because doing so removes platelets clumps resulting from incomplete resuspension of the concentrated platelets.

When all of the resuspended platelets to be filtered have passed through the size exclusion filter 26, the controller reconfigures the valves of the hardware apparatus 12 to define a different flow path through the cassette 16c. The new valve configuration defines a flow path through the cassette 16c between the tubing segment 44 connected to the additive container 46 and the second tubing segment 32 (as in FIG. 5) or between some other source of additive (e.g., a separate plasma container) and the second tubing segment 32.

The controller operates one or more of the pumps of the hardware apparatus 12 to convey additive from the additive source, into and through the cassette 16c, and out of the cassette 16c via the second tubing segment 32. The additive flows through the size exclusion filter 26 and into the platelet storage container(s) 28, where it mixes with the filtered resuspended platelets as a final platelet product. If a plurality of additive containers are provided, additive from the different containers may be sequentially or simultaneously conveyed through the size exclusion filter 26. As described previously, flushing the size exclusion filter 26 with the additive improves platelet recovery in the final platelet product by displacement of resuspended platelets with the additive and may also break up platelet clumps that may be present in the size exclusion filter 26, thereby increasing platelet yield.

With a suitable amount of additive in the platelet storage container(s) 28, the procedure may end or continue with additional processing.

ASPECTS

Aspect 1. A disposable processing circuit configured for use in combination with a reusable hardware apparatus including a separation device, the processing circuit comprising: a processing chamber configured to receive a fluid including plasma and platelets and associable with a separation device of a reusable hardware apparatus for separation of platelets from at least a portion of another constituent of a fluid including plasma and platelets; a size exclusion filter in downstream fluid communication with the processing chamber and configured to remove platelet clumps from separated platelets conveyed therethrough from the processing chamber; a platelet storage container in downstream fluid communication with the size exclusion filter and configured to receive filtered platelets from the size exclusion filter; and an additive container in upstream fluid communication with the size exclusion filter.

Aspect 2. The disposable processing circuit of Aspect 1, further comprising a cassette, wherein the processing chamber and the additive container are in fluid communication with the size exclusion filter through the cassette.

Aspect 3. The disposable processing circuit of any one of the preceding Aspects, wherein the size exclusion filter is connected to the platelet storage container by a tubing segment.

Aspect 4. The disposable processing circuit of any one of the preceding Aspects, wherein the additive container includes a synthetic platelet storage media.

Aspect 5. The disposable processing circuit of any one of Aspects 1-3, wherein the additive container is configured to receive plasma from the processing chamber.

Aspect 6. A system for the collection of platelets, comprising: the disposable processing circuit of any one of the preceding Aspects; and a reusable hardware apparatus including a separation device and a controller, wherein the controller is programmed to operate the hardware apparatus to convey a fluid including plasma and platelets into the processing chamber, separate platelets from at least a portion of another constituent of the fluid in the processing chamber using the separation device, convey the separated platelets through the size exclusion filter to remove platelet clumps from the separated platelets, collect the filtered platelets in the platelet storage container, and convey an additive from the additive container through the size exclusion filter and into the platelet storage container.

Aspect 7. The system of Aspect 6, wherein the separation device comprises a centrifuge.

Aspect 8. The system of any one of Aspects 6-7, wherein the controller is further programmed to operate the hardware apparatus to draw whole blood into the processing circuit from a blood source, and said fluid comprises anticoagulated whole blood.

Aspect 9. The system of any one of Aspects 6-8, wherein said at least a portion of another constituent of the fluid comprises red blood cells.

Aspect 10. A method for collecting platelets comprising: providing a fluid from a fluid source including plasma and platelets; separating platelets from at least a portion of another constituent of the fluid; conveying the separated platelets through a size exclusion filter to remove platelet clumps from the separated platelets; collecting the filtered platelets in a platelet storage container; and conveying an additive through the size exclusion filter and into the platelet storage container.

Aspect 11. The method of Aspect 10, wherein said separating platelets from at least a portion of another constituent of the fluid comprises separating platelet-rich plasma from said at least a portion of another constituent of the fluid, and the separated platelets comprise platelet-rich plasma.

Aspect 12. The method of Aspect 10, wherein said separating platelets from at least a portion of another constituent of the fluid comprises separating platelet-rich plasma from said at least a portion of another constituent of the fluid, separating the platelet-rich plasma into concentrated platelets and platelet-poor plasma, and resuspending the concentrated platelets, and the separated platelets comprise resuspended platelets.

Aspect 13. The method of any one of Aspects 10-12, wherein the separated platelets are separated from the at least a portion of another constituent of the fluid by centrifugation.

Aspect 14. The method of any one of Aspects 10-13, wherein the fluid comprises anticoagulated whole blood and said at least a portion of another constituent of the fluid comprises red blood cells.

Aspect 15. The method of any one of Aspects 10-14, employing the system of any one of Aspects 6-9.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A disposable processing circuit configured for use in combination with a reusable hardware apparatus including a separation device, the disposable processing circuit comprising:
   a processing chamber configured to receive a fluid including plasma and platelets and associable with said separation device of said reusable hardware apparatus for separation of platelets from at least a portion of another constituent of said fluid including said plasma and platelets;
   a size exclusion filter including an upstream end and a single outlet, wherein
      the upstream end of the size exclusion filter is in downstream fluid communication with the processing chamber, and
      the size exclusion filter is configured to remove platelet clumps from separated platelets conveyed therethrough from the processing chamber via the upstream end, with filtered platelets exiting the size exclusion filter via the outlet;
   a platelet storage container in downstream fluid communication with the outlet of the size exclusion filter and configured to receive the filtered platelets exiting from the size exclusion filter via the outlet; and
   an additive container in upstream fluid communication with the upstream end of the size exclusion filter, wherein the disposable processing circuit defines a fluid flow path extending from the processing chamber to the platelet storage container, with the fluid flow path including the size exclusion filter and not including a leukoreduction filter and being configured such that a flow of an additive from the additive container into the size exclusion filter via the upstream end, through the size exclusion filter, and out of the size exclusion filter via the outlet will break up the platelet clumps retained in the size exclusion filter, wherein the additive is separated plasma.

2. The disposable processing circuit of claim 1, further comprising a cassette, wherein the processing chamber and the additive container are in fluid communication with the size exclusion filter through the cassette.

3. The disposable processing circuit of claim 1, wherein the size exclusion filter is connected to the platelet storage container by a tubing segment.

4. The disposable processing circuit of claim 1, wherein the additive container is configured to receive said separated plasma from the processing chamber.

5. The disposable processing circuit of claim 1, wherein
the processing chamber comprises a first stage and a second stage, and
the plasma is platelet-poor plasma conveyed into the additive container from the second stage of the processing chamber.

6. A system for collection of platelets, comprising:
a disposable processing circuit including
a processing chamber,
a size exclusion filter including
an upstream end in downstream fluid communication with the processing chamber, and
a single outlet,
a platelet storage container in downstream fluid communication with the outlet of the size exclusion filter, and
an additive container in upstream fluid communication with the upstream end of the size exclusion filter, wherein the disposable processing circuit defines a fluid flow path extending from the processing chamber to the platelet storage container, with the fluid flow path including the size exclusion filter and not including a leukoreduction filter; and
a reusable hardware apparatus including a separation device and a controller, wherein the controller is configured to operate the hardware apparatus to
convey a fluid including plasma and platelets into the processing chamber,
separate said platelets from at least a portion of another constituent of the fluid in the processing chamber using the separation device,
convey separated platelets into the size exclusion filter via the upstream end, through the size exclusion filter to remove platelet clumps from the separated platelets, and out of the size exclusion filter via the outlet as filtered platelets,
collect the filtered platelets exiting the outlet of the size exclusion filter in the platelet storage container, and
convey an additive from the additive container into the size exclusion filter via the upstream end, through the size exclusion filter, out of the size exclusion filter via the outlet, and into the platelet storage container so as to break up the platelet clumps retained in the size exclusion filter, wherein the additive is separated plasma.

7. The system of claim 6, wherein the separation device comprises a centrifuge.

8. The system of claim 6, wherein
the controller is further configured to operate the hardware apparatus to draw whole blood into the processing circuit from a blood source, and
said fluid comprises anticoagulated whole blood.

9. The system of claim 6, wherein said at least a portion of another constituent of the fluid comprises red blood cells.

10. The system of claim 6, wherein the disposable processing circuit further includes a cassette, with the processing chamber and the additive container being in fluid communication with the size exclusion filter through the cassette.

11. The system of claim 6, wherein the size exclusion filter is connected to the platelet storage container by a tubing segment.

12. The system of claim 6, wherein the additive comprises said separated plasma conveyed into the additive container from the processing chamber.

13. The system of claim 6, wherein
the processing chamber comprises a first stage and a second stage, and
the plasma is platelet-poor plasma conveyed into the additive container from the second stage of the processing chamber.

14. A method for collecting platelets using a processing circuit defining a fluid flow path extending from a processing chamber to a platelet storage container, the method comprising:
providing a fluid from a fluid source including plasma and platelets;
separating said platelets from at least a portion of another constituent of the fluid in the processing chamber;
conveying separated platelets into a size exclusion filter via an upstream end of the size exclusion filter, through the size exclusion filter to remove platelet clumps from the separated platelets, and out of the size exclusion filter as filtered platelets via a single outlet of the size exclusion filter;
collecting the filtered platelets exiting the outlet of the size exclusion filter in the platelet storage container; and
conveying an additive into the size exclusion filter via the upstream end, through the size exclusion filter, out of the size exclusion filter via the outlet, and into the platelet storage container so as to break up the platelet clumps retained in the size exclusion filter, with the fluid flow path including the size exclusion filter and not including a leukoreduction filter and with the additive being separated plasma.

15. The method of claim 14, wherein
said separating said platelets from at least a portion of another constituent of the fluid comprises separating platelet-rich plasma from said at least a portion of another constituent of the fluid, and
the separated platelets comprise the platelet-rich plasma.

16. The method of claim 14, wherein
said separating said platelets from at least a portion of another constituent of the fluid comprises
separating platelet-rich plasma from said at least a portion of another constituent of the fluid,
separating the platelet-rich plasma into concentrated platelets and platelet-poor plasma, and
resuspending the concentrated platelets, and
the separated platelets comprise resuspended platelets.

17. The method of claim 14, wherein the separated platelets are separated from the at least a portion of another constituent of the fluid by centrifugation.

18. The method of claim 14, wherein the fluid comprises anticoagulated whole blood and said at least a portion of another constituent of the fluid comprises red blood cells.

19. The method of claim 14, wherein the additive is separated from the fluid.

20. The method of claim 14, wherein
the processing chamber comprises a first stage and a second stage,
said separating said platelets from at least a portion of another constituent of the fluid in the processing chamber includes separating said platelets from platelet-poor plasma in the second stage of the processing chamber, and
the plasma is the platelet-poor plasma from the second stage of the processing chamber.

* * * * *